United States Patent
Mauch et al.

(10) Patent No.: US 8,292,948 B2
(45) Date of Patent: Oct. 23, 2012

(54) APPARATUS AND METHODS FOR CREATING A VENOUS VALVE FROM AUTOLOGOUS TISSUE

(75) Inventors: Kevin Mauch, Windsor, CA (US); Melissa Jeffries, Los Angeles, CA (US); Ryan Bienvenu, Santa Rosa, CA (US); Maria Arreguin, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 149 days.

(21) Appl. No.: 12/706,900

(22) Filed: Feb. 17, 2010

(65) Prior Publication Data

US 2011/0202124 A1   Aug. 18, 2011

(51) Int. Cl.
*A61F 2/06* (2006.01)
(52) U.S. Cl. ....................................................... 623/1.24
(58) Field of Classification Search ................. 623/1.24, 623/2.1, 2.17, 2.18
See application file for complete search history.

(56) References Cited

U.S. PATENT DOCUMENTS

| 5,358,518 | A | * | 10/1994 | Camilli | 623/1.24 |
| 5,413,584 | A | | 5/1995 | Schulze | |
| 5,569,245 | A | | 10/1996 | Guglielmi et al. | |
| 5,624,449 | A | | 4/1997 | Pham et al. | |
| 5,810,847 | A | * | 9/1998 | Laufer et al. | 606/142 |
| 6,241,763 | B1 | * | 6/2001 | Drasler et al. | 623/1.24 |
| 6,902,576 | B2 | | 6/2005 | Drasler et al. | |
| 7,007,698 | B2 | * | 3/2006 | Thornton | 128/898 |
| 7,416,557 | B2 | * | 8/2008 | Drasler et al. | 623/1.11 |
| 2003/0191479 | A1 | * | 10/2003 | Thornton | 606/151 |
| 2004/0193253 | A1 | | 9/2004 | Thorpe et al. | |
| 2004/0215339 | A1 | * | 10/2004 | Drasler et al. | 623/3.1 |
| 2004/0220593 | A1 | | 11/2004 | Greenhalgh | |
| 2006/0089708 | A1 | | 4/2006 | Osse et al. | |
| 2007/0112423 | A1 | * | 5/2007 | Chu | 623/2.11 |
| 2008/0046071 | A1 | * | 2/2008 | Pavcnik | 623/1.24 |

FOREIGN PATENT DOCUMENTS

| WO | WO2004/037128 | 5/2004 |
| WO | WO2004/064648 | 8/2004 |

* cited by examiner

*Primary Examiner* — Paul Prebilic
*Assistant Examiner* — Leslie Coburn

(57) ABSTRACT

An implantable prosthesis for percutaneous placement within a vein that forces opposing portions of the vessel wall of a vein together to create a new valve of autologous vein tissue to be operable to alternate between a valve closed configuration and a valve open configuration. When in a preset closed configuration, the implantable prosthesis pushes or pulls portions of the vessel wall of the vein together to substantially close the vein lumen and prevent retrograde blood flow from backflowing through the new valve in the valve closed configuration. The implantable prosthesis has leg portions that may be pushed apart in response to antegrade blood flow through the vein to allow the new valve to achieve the valve open configuration.

16 Claims, 13 Drawing Sheets

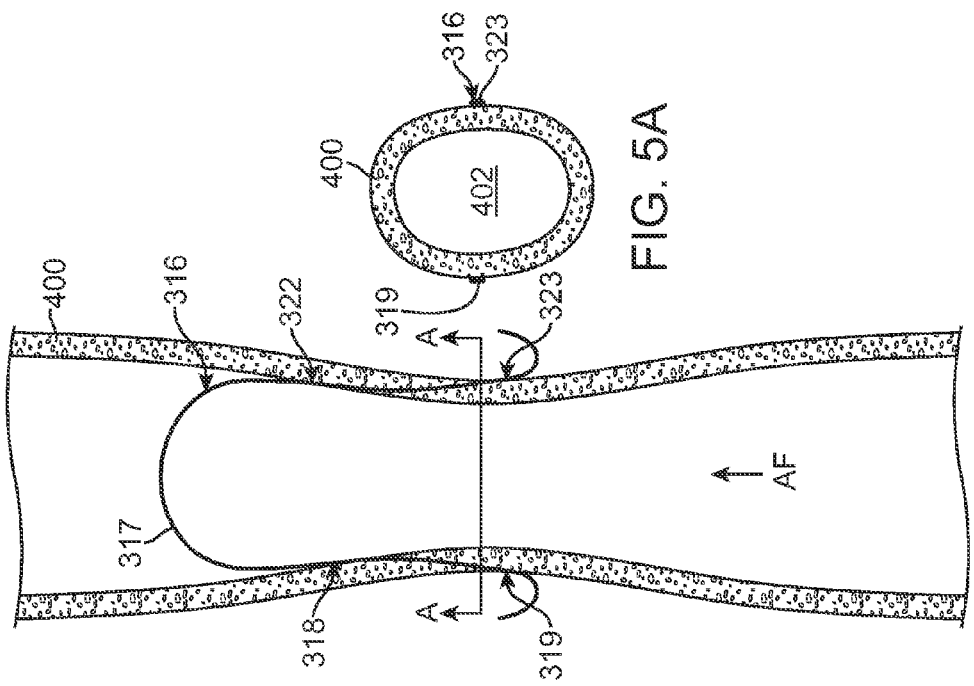
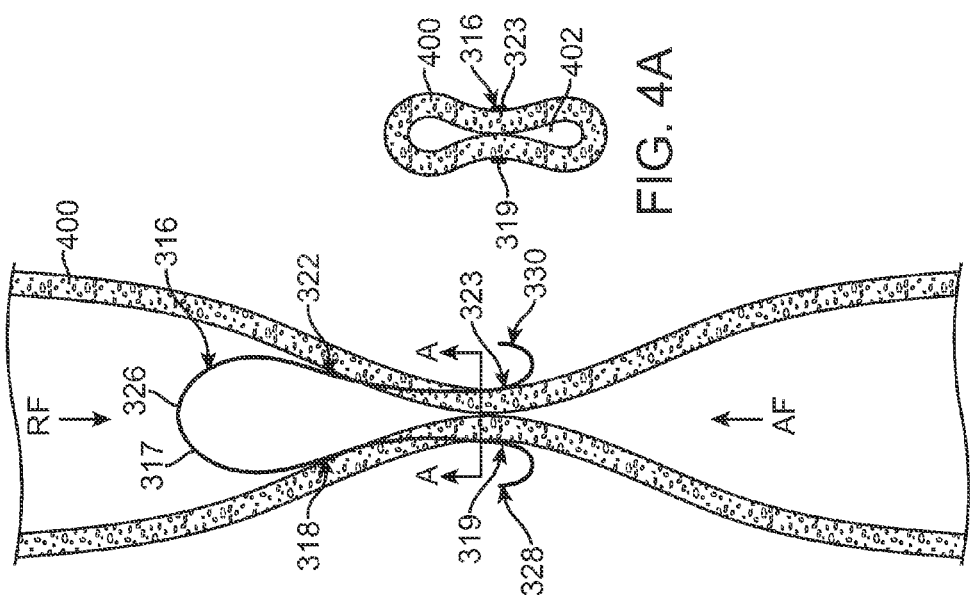

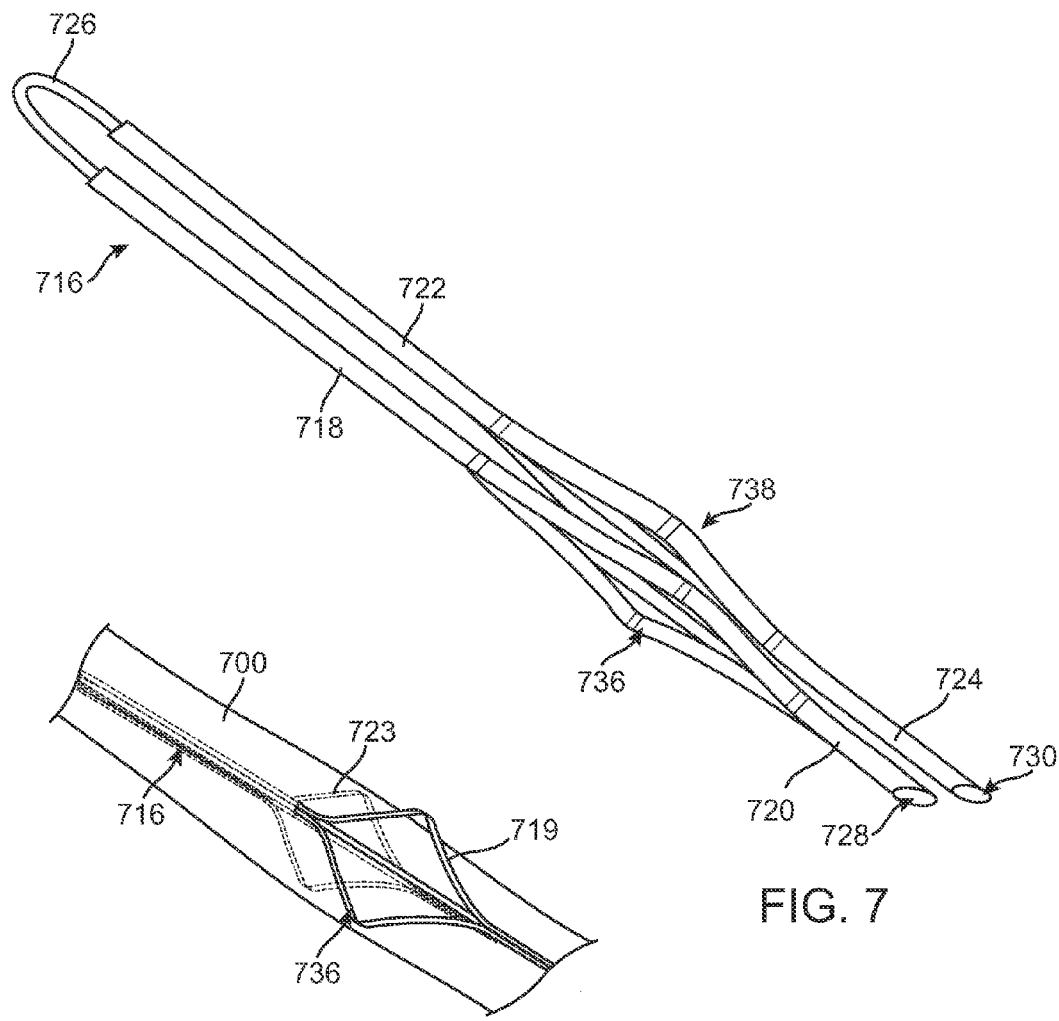
FIG. 7
FIG. 8A
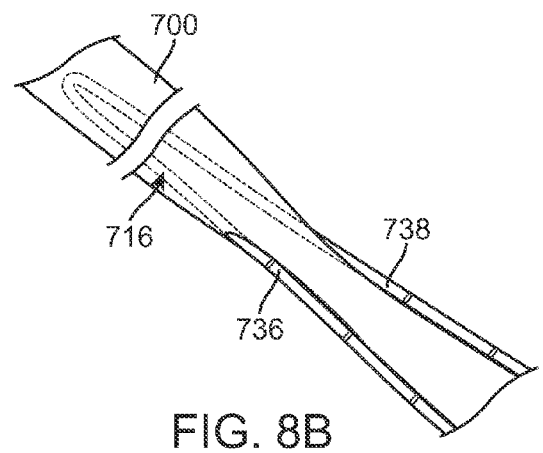
FIG. 8B

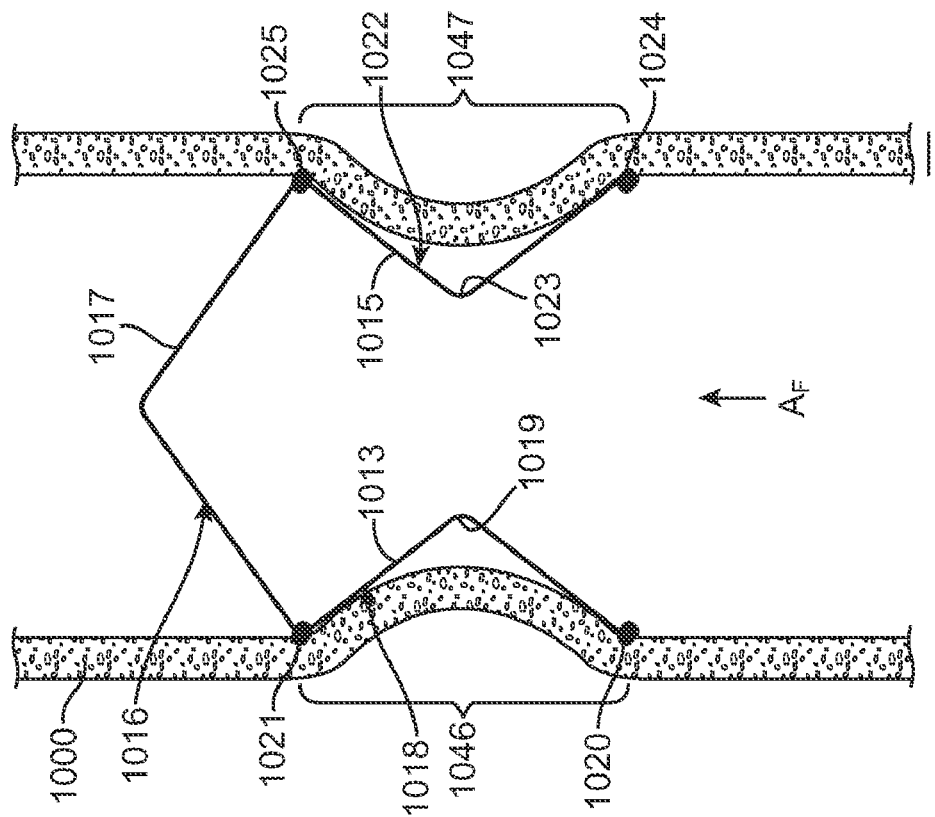
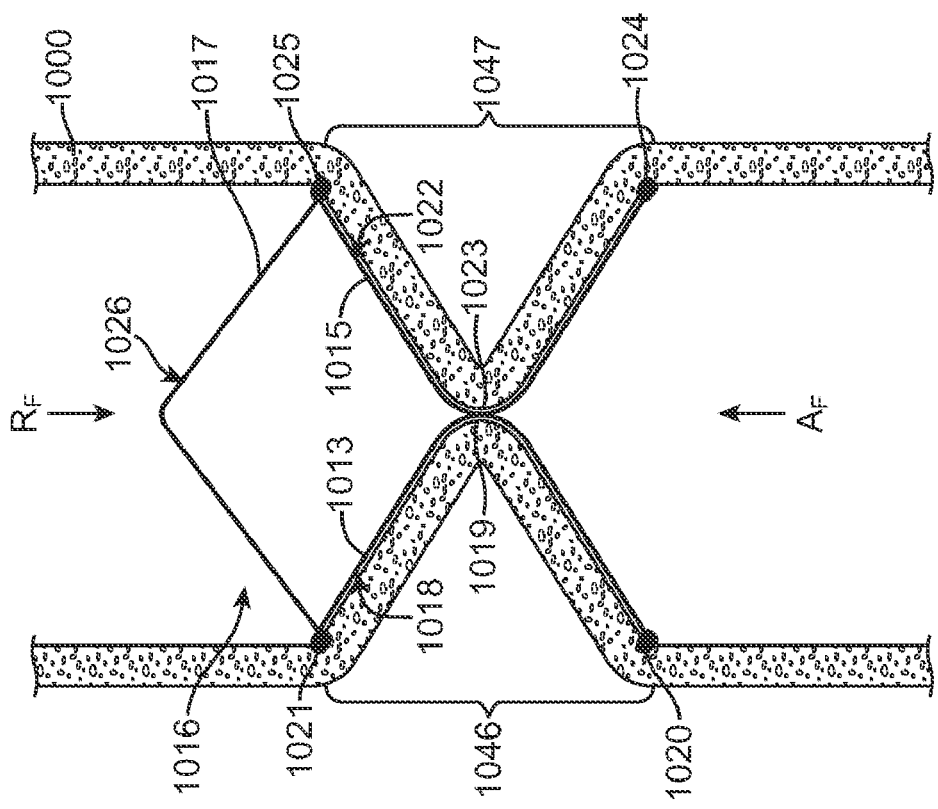

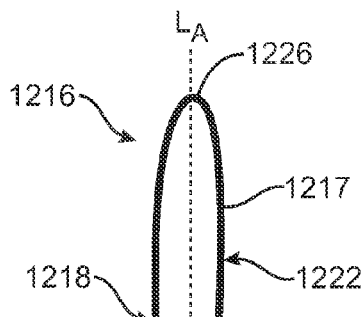
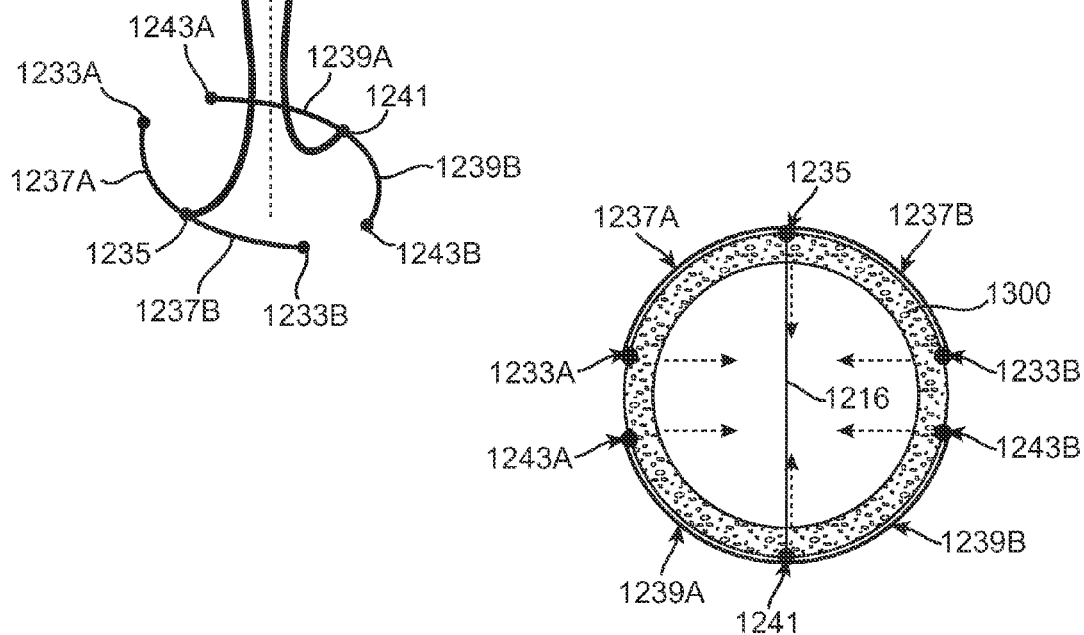
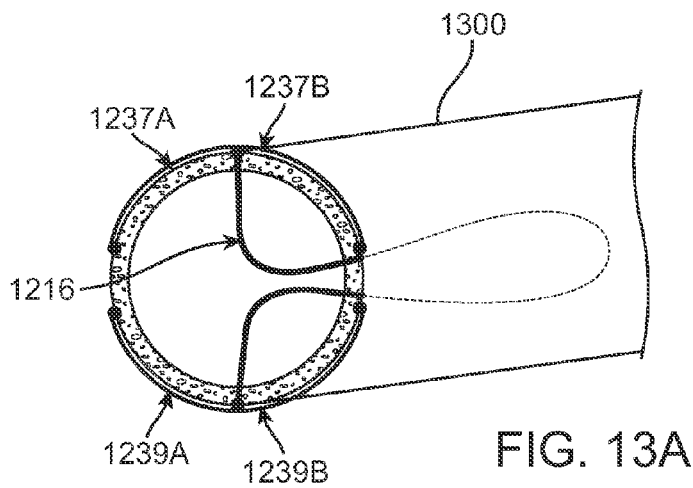

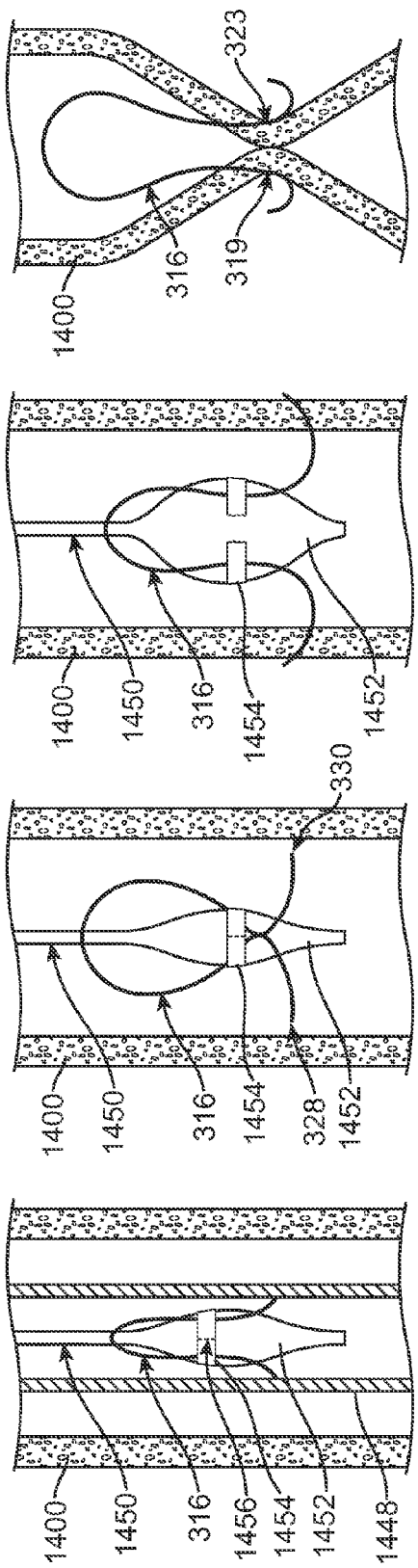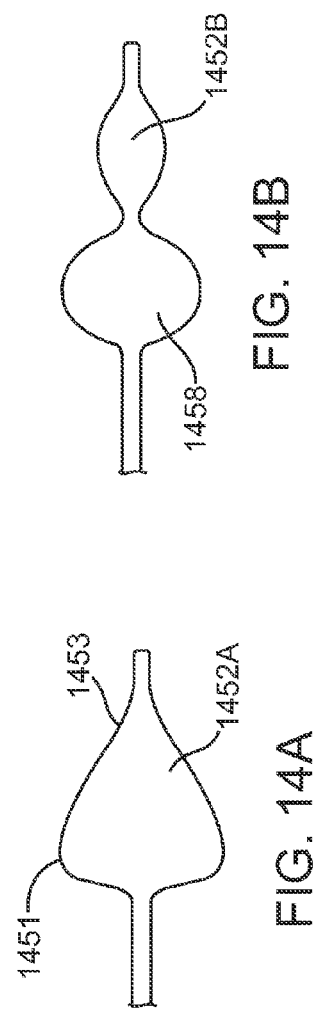

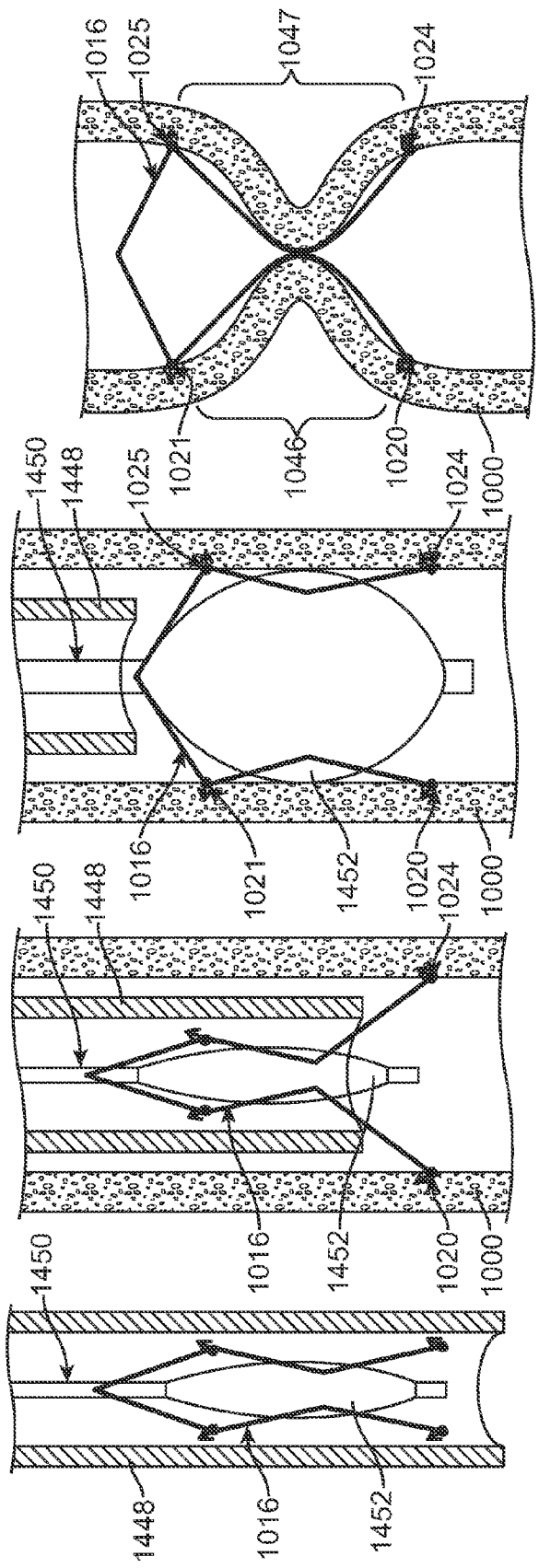

APPARATUS AND METHODS FOR CREATING A VENOUS VALVE FROM AUTOLOGOUS TISSUE

FIELD OF THE INVENTION

The invention relates to apparatus and methods for percutaneously creating a one-way venous valve in vivo from autologous tissue.

BACKGROUND OF THE INVENTION

Venous valves are found within native venous vessels and are used to assist in returning blood back to the heart in an antegrade direction from all parts of the body. The venous system of the leg for example includes the deep venous system and the superficial venous system, both of which are provided with venous valves which are intended to direct blood toward the heart and prevent backflow or retrograde flow which can lead to blood pooling or stasis in the leg. Incompetent valves can also lead to reflux of blood from the deep venous system to the superficial venous system and the formation of varicose veins. Superficial veins which include the greater and lesser saphenous veins have perforating branches in the femoral and popliteal regions of the leg that direct blood flow toward the deep venous system and generally have a venous valve located near the junction with the deep system. Deep veins of the leg include the anterior and posterior tibial veins, popliteal veins, and femoral veins. Deep veins are surrounded in part by musculature tissues that assist in generating flow due to muscle contraction during normal walking or exercising. Venous pressure in lower leg veins of a healthy person may range from 0 mm Hg to over 200 mm Hg, depending on factors such as the activity of the body, i.e., stationary or exercising, the position of the body, i.e., supine or standing, and the location of the vein, i.e., ankle or thigh. For example, venous pressure may be approximately 80-90 mm Hg while standing and may be reduced to 60-70 mm Hg during exercise. Despite exposure to such pressures, the valves of the leg are very flexible and can close with a pressure drop of less than one mm Hg.

FIGS. 1A-1B are schematic representations of blood flow through a healthy native valve 104 within a vein 100. Valves within the venous system are configured in a variety of shapes that depend on anatomical location, vessel size, and function. For example, the shape of the venous valve may include leaflets or leaflets with sinuses. The natural venous valve leaflet configuration referenced herein is for clarity of function and is not limiting in the application of the referenced embodiments. Venous valve 104 controls blood flow through lumen 102 of vein 100 via leaflets 106, 108. More particularly, venous valve 104 opens to allow antegrade flow 112 through leaflets 106, 108 as shown in FIG. 1A. Venous valve 104 closes to prevent retrograde flow or backflow 114 through leaflets 106, 108 as shown in FIG. 1B.

Veins typically located in the leg can become distended from prolonged exposure to excessive pressure and due to weaknesses found in the vessel wall causing the natural venous valves to become incompetent leading to retrograde blood flow in the veins. Such incompetent valves no longer function to help pump or direct the blood back to the heart during normal walking or use of the leg muscles. As a result, blood tends to pool in the lower leg and can lead to leg swelling and the formation of deep venous thrombosis and phlebitis. The formation of thrombus in the veins can further impair venous valvular function by causing valvular adherence to the venous wall with possible irreversible loss of venous function. Continued exposure of the venous system to blood pooling and swelling of the surrounding tissue can lead to post phlebitic syndrome with a propensity for open sores, infection, and may lead to limb amputation.

Chronic Venous Insufficiency (CVI) occurs in patients that have deep and superficial venous valves of their lower extremities (distal to their pelvis) that have failed or become incompetent due to congenital valvular abnormalities and/or pathophysiologic disease of the vasculature. As a result, such patients suffer from varicose veins, swelling and pain of the lower extremities, edema, hyper pigmentation, lipodermatosclerosis, and deep vein thrombosis (DVT). Such patients are at increased risk for development of soft tissue necrosis, ulcerations, pulmonary embolism, stroke, heart attack, and amputations.

FIG. 2 is a schematic representation of blood flow through an incompetent venous valve. Valve leaflets 106, 108 do not completely close and thus allow some venous blood to flow in a retrograde direction. The backflow 114 leaks through venous valve 104 creating blood build-up that eventually may destroy the venous valve and cause a distended area or venous wall bulge 110. More specifically, the vessel wall of vein 100 expands into a pouch or bulge, such that the vessel has a knotted appearance when the pouch is filled with blood. As the bulging progresses, vein 100 becomes further enlarged and valve leaflets 106, 108 move farther apart, allowing even more blood to backflow. Thus, once valve 104 becomes incompetent, the venous insufficiency/incompetency progressively worsens. The distended vessel wall area may occur on the outflow side of the valve above leaflets 106, 108 as shown in FIG. 2, and/or on the inflow side of the valve below leaflets 106, 108. After a vein segment becomes incompetent, the vessel wall dilates and fluid velocity there through decreases, which may lead to flow stasis and thrombus formation in the proximity of the venous valve.

Repair and replacement of venous valves presents a formidable challenge due to the low blood flow rate found in native veins, the very thin wall structure of the venous wall and the venous valve, and the ease and frequency of which venous blood flow can be impeded or totally blocked for a period of time. Surgical reconstruction techniques used to address venous valve incompetence include venous valve bypass using a segment of vein with a competent valve, venous transposition to bypass venous blood flow through a neighboring competent valve, and valvuloplasty to repair the valve cusps. These surgical approaches may involve placement of synthetic, allograft and/or xenograft prostheses inside of or around the vein. However, such prostheses have not been devoid of problems, such as thrombus formation and valve failure due to leaflet thickening/stiffening, non-physiologic flow conditions, non-biocompatible materials and/or excessive dilation of the vessels with a subsequent decrease in blood flow rates. In addition, many venous valve prostheses include leaflets and/or hinged flaps and are similar to valves placed into the heart, which are complex and designed for high blood pressures and flow associated with the heart instead of lower venous blood pressures and flow associated with veins in the lower extremities.

Percutaneous methods for treatment of venous insufficiency are being studied, some of which include placement of synthetic, allograft and/or xenograft prosthesis that suffer from similar problems as the surgically implanted ones discussed above.

In addition, venous valve formation from autologous tissue has been disclosed in U.S. Pat. No. 6,902,576 to Drasler et al. Drasler et al. suggests use of autologous tissue with blood contact of an endothelial layer to eliminate biocompatability issues and also alleviate thrombus formation due to low flow. However, methods of in situ venous valve formation according to Drasler et al. are surgical in nature and involve reshaping a distended, diseased vein, which carries with it the risk of rupture or tearing of the thin-walled structure.

In light of these limitations, there is a need for an improved device to restore normal venous circulation to patients suffering from venous valve insufficiency. The present disclosure is directed to a simple prosthesis that may be used in percutaneous, minimally invasive procedures to create a venous valve in vivo from autologous vein tissue.

BRIEF SUMMARY OF THE INVENTION

Embodiments hereof are directed to an implantable prosthesis for creating a venous valve of autologous tissue. In a preset closed configuration, the prosthesis forces opposing portions of a vein wall together to create a valve of autologous vein tissue to substantially prevent retrograde blood flow through the valve. The prosthesis assumes a temporary open configuration in response to antegrade blood flow through the vein.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 4 is a schematic representation of the valve creation device of FIG. 3 implanted within a vein, wherein the valve creation device is in its closed or preset configuration.

FIG. 4A is a cross-sectional view taken along line A-A of FIG. 4.

FIG. 5 is a schematic representation of the valve creation device of FIG. 3 implanted within a vein, wherein the valve creation device is in its open configuration.

FIG. 5A is a cross-sectional view taken along line A-A of FIG. 5.

FIG. 7 is a perspective view of a valve creation device according to another embodiment hereof.

FIG. 8A is a side view of the valve creation device of FIG. 7 implanted within a vein.

FIG. 8B is a top view of the valve creation device of FIG. 7.

FIG. 10 is a schematic representation of a valve creation device according to another embodiment hereof, wherein the device is implanted within a vein and is in its closed or preset configuration.

FIG. 11 is a schematic representation of the valve creation device of FIG. 10 implanted within a vein, wherein the valve creation device is in its open configuration.

FIG. 12 is a perspective view of a valve creation device according to another embodiment hereof wherein the valve creation device is in the open configuration.

FIG. 13 is a cross-sectional view of the valve creation device of FIG. 12 placed within a vein, wherein the valve creation device is in the open configuration.

FIG. 13A is a schematic representation of the valve creation device of FIG. 12 placed within a vein, wherein the valve creation device is in the open configuration.

FIGS. 14, 15, 16, and 17 are schematic representations of a method of percutaneously placing a valve creation device within a vein to create a valve from autologous vein tissue according to an embodiment hereof.

FIG. 14A and FIG. 14 are schematic representations of alternate configurations for the delivery system of FIGS. 14-17 according to an embodiment hereof.

FIGS. 21-24 are schematic representations of a method of percutaneously placing the valve creation device of FIGS. 10-11 within a vein to create a valve from autologous vein tissue according to an embodiment hereof.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the veins, the invention may also be used in any other body passageways where it is deemed useful. Furthermore, there is no intention to be bound by any expressed or implied theory presented in the preceding technical field, background, brief summary or the following detailed description.

Figure 1A:
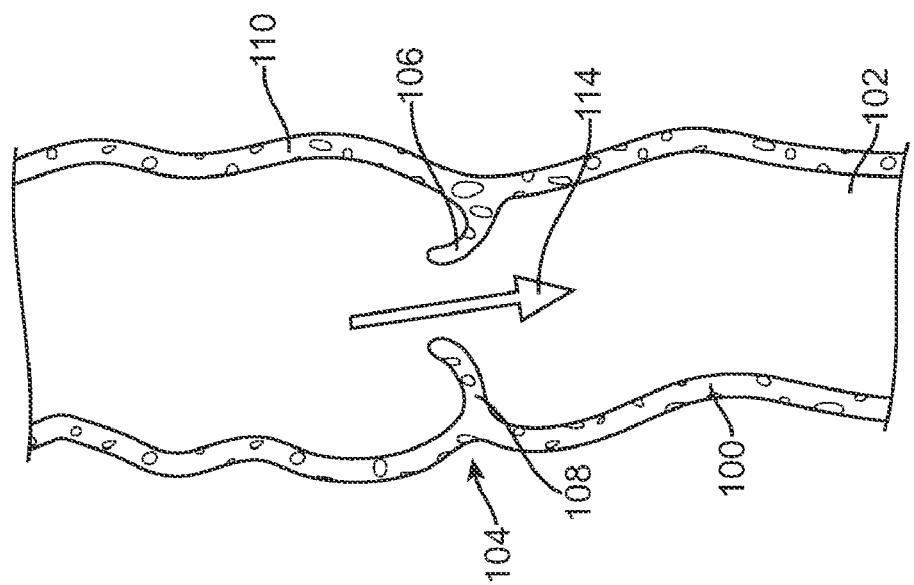
FIGS. 1A-1B are schematic representations of blood flow through a healthy valve within a vein.
Figure 1B:
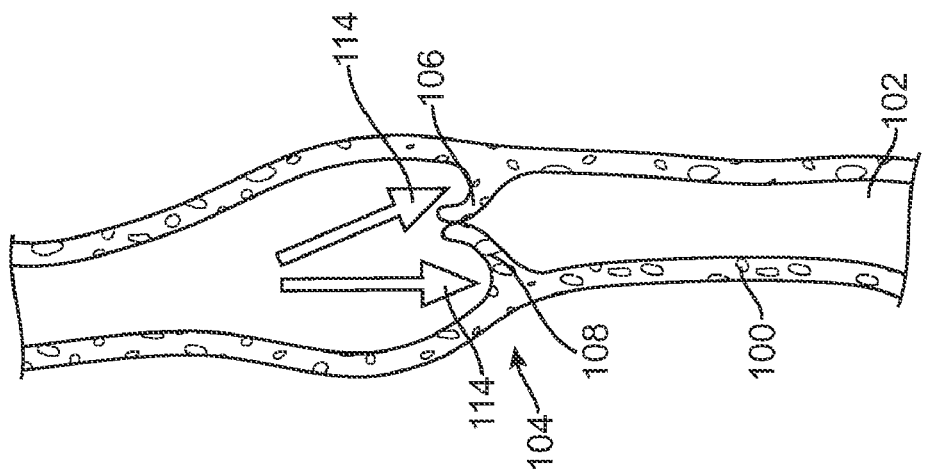
Figure 2:
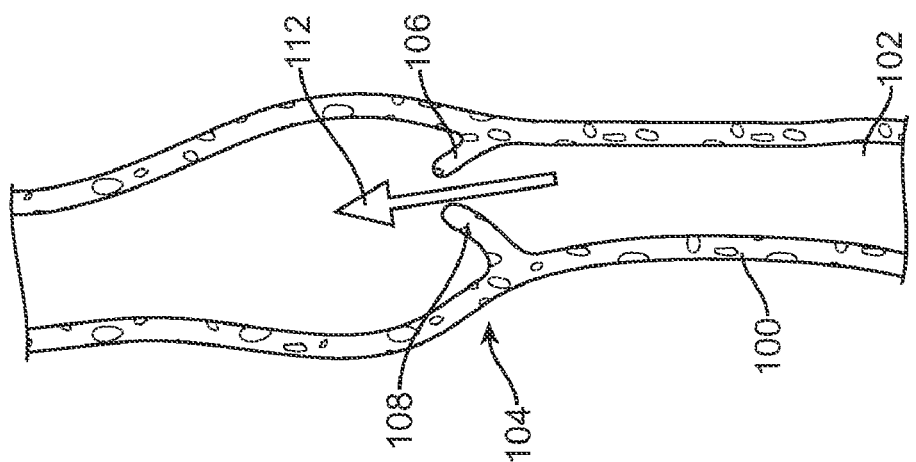
FIG. 2 is a schematic representation of blood flow through an incompetent valve within a vein.
Figure 3:
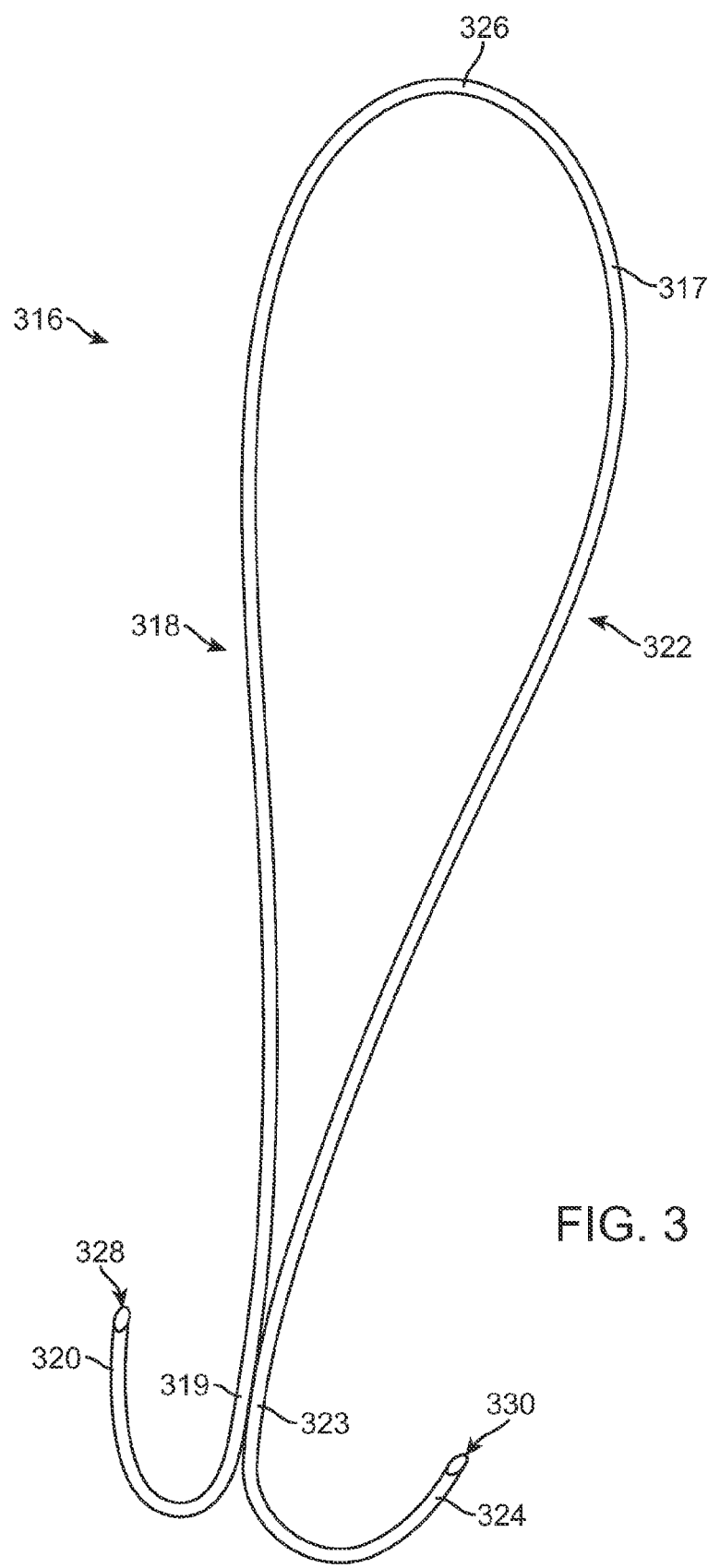
FIG. 3 is a perspective view of a valve creation device according to an embodiment hereof.

Referring to FIGS. 3-5, an implantable prosthesis or valve creation device 316 for treating chronic venous insufficiency according to an embodiment hereof is shown. In creating a valve that controls the flow of blood through a vein from autologous vein tissue, valve creation device 316 may be considered a scaffolding or support framework that opens and closes opposing portions of the vessel wall in response to antegrade and retrograde blood flow, i.e., pressure differentials across the newly created valve, to mimic venous valve operation. Valve creation device 316 is an implantable prosthesis formed from a wire-like or tubular structure 317 of a biocompatible resilient material such as nitinol, 316L stainless steel, MP35N spring wire, an acetal copolymer, or a polymeric material having shape memory characteristics. In various embodiments in accordance herewith, wire-like structure 317 may be solid or hollow and have a circular cross-section. By minimizing the cross-section of wire-like structure 317, the amount of foreign material implanted in the body and the interruption or footprint of the implant relative to blood flow is minimized to avoid thrombosis. In one embodiment, wire-like structure 317 has a diameter less than 0.10 inches. In one embodiment, wire-like structure 317 has a diameter between 0.006 inches-0.040 inches. In another embodiment, the cross-section of wire-like structure 317 may be an oval, square, rectangular, or any other suitable shape.

Figure 26:
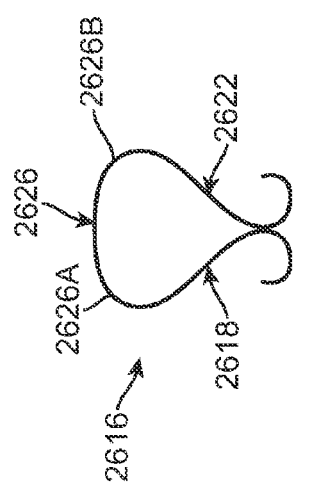
FIG. 26 is a schematic representation of a valve creation device according to another embodiment hereof.
Figure 27:
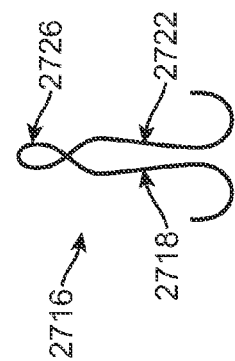
FIG. 27 is a schematic representation of a valve creation device according to another embodiment hereof.

Wire-like structure 317 is shaped to include a first leg 318, a second leg 322, and a biasing member 326 extending from first leg 318 to second leg 322. As shown in FIG. 3, biasing member 326 is a curved segment integrally formed with and positioned between first leg 318 and second leg 322 such that valve creation device 316 is a unitary structure formed out of a single piece of material. Biasing member 326 biases first leg 318 and second leg 322 towards each other due to the material's inherent spring restorative forces. In an embodiment, biasing member 326 may be U-shaped and legs 318, 322 may be mirror images of each other. In another embodiment, the valve creation device may include a biasing member that is a separate component that is attached to the first and second legs by any suitable manner known in the art such as for example welding, including resistance welding, friction welding, laser welding or another form of welding, soldering, using an adhesive, adding a connecting element there between, or by another mechanical method. Rather than an arc or curved segment, the biasing member may have alternative configurations that bias first leg 318 and second leg 322 towards each other and impart spring characteristics to the valve creation device. For example, FIG. 26 illustrates a valve creation device 2616 resembling a binder clip having an elongated biasing member 2626 extending from a first leg 2618 to a second leg 2622. The rounded corners or ends 2626A, 2626B of biasing member 2626 straddle or span across the vessel lumen of the vein in situ. In another example shown in FIG. 27, a valve creation device 2716 has a looped biasing member 2726 connecting a first leg 2718 to a second leg 2722. In another embodiment (not shown), the biasing member may be an asymmetric curved segment such that the valve creation device resembles a bobby pin.

In the embodiment shown in FIG. 3, end portions 320, 324 of first and second legs 318, 322, respectively, include sharpened or pointed tips 328, 330, respectively, that are operable to pierce and penetrate through opposing portions of the vessel wall of a vein. In addition, end portions 320, 324 may be curved or hooked as shown to secure valve creation device 316 within the vein. The hooked configuration ensures that end portions 320, 324 remain on the outer or exterior surface of the vein wall and prevent tips 328, 330 from incidentally becoming dislodged and/or pushed into the vein resulting in a possible embolization. More specifically, hooked end portions 320, 324 are intended to prevent valve creation device 316 from being pushed out of position by the antegrade flow passing across the portion of valve creation device 316 in the lumen.

Wire-like structure 317 is formed from a biocompatible resilient material and has an inherent spring restorative force or mechanical memory to return to its original preset shape, shown in FIG. 3, after being loaded. "Resilient" and "resilience" as used herein to refer to a material that is capable of recovering an original preset shape or form after being elastically stretched, deformed, compressed, or the like. Valve creation device 316 is operable to alternate between the preset closed configuration shown in FIG. 3, which when implanted creates a valve closed configuration as shown in FIGS. 4 and 4A, and an open configuration, which when subjected to antegrade flow in situ creates a valve open or flow configuration as shown in FIGS. 5 and 5A. Mechanical memory may be imparted to wire-like structure 317 by thermal treatment to achieve a spring temper in stainless steel, for example, or to set a shape memory in a susceptible metal alloy, such as nitinol. For example, wire-like structure 317 of valve creation device 316 may be shape-set into the closed configuration using an oven set to an appropriate temperature for the material, by e.g., approximately 525° C. for nitinol although the temperature will vary depending on the material of wire-like structure 317. When valve creation device 316 is in the preset closed configuration, a contact portion 319 of first leg 318 and a contact portion 323 of second leg 322 are biased or pressed toward each other due to biasing member 326, such that when valve creation device 316 is implanted within a vein as further described below the valve creation device will operably force opposing sites or points on the vessel wall of a vein together to create a new valve of autologous vein tissue. In another embodiment hereof (not shown), in the preset closed configuration, contact portion 319 of first leg 318 may pass over or overlap contact portion 323 of second leg 322 to operably force opposing sites on the vessel wall of a vein together. In situ, antegrade blood flow acts against the new valve, overcomes the spring restorative force of wire-like structure 317, and forces contact portions 319, 323 of valve creation device 316 apart to achieve the valve open configuration of FIG. 5 that allows blood flow through the new valve. When blood flow through the vein changes direction, i.e., antegrade blood flow and pressure is reduced and retrograde blood flow occurs due to changing pressure differentials across the new valve, the spring restorative force of wire-like structure 317 takes over and causes valve creation device 316 to revert back to the preset closed configuration to thereby achieve the valve closed configuration of FIG. 4 that prevents blood from backflowing through the new valve. The relatively simple construction of valve creation device 316 does not include leaflets or hinged flaps that may thicken, tear or fail, avoids tissue ingrowth of such leaflets, and also avoids pooling of blood within such leaflets that may result in clots.

More particularly, FIGS. 4, 4A, 5 and 5A are schematic representations of how valve creation device 316 forms a new venous valve from autologous tissue and alternates between its preset closed configuration and its open configuration to regulate blood flow through the new venous valve. FIG. 4 is a schematic view of valve creation device 316 in its preset closed configuration placed within a vein 400 having an incompetent native valve (not shown). Valve creation device 316 is delivered to and deployed within vein 400 in a percutaneous manner, as will be described in more detail below, and is positioned at a target location within lumen 402 of vein 400 where a new vein valve is to be created. Initially luminal access to a desired peripheral vein 400, such as the greater or lesser saphenous, femoral, or popliteal veins, is obtained using standard percutaneous techniques. It should be understood by one of skill in the art that methods as described herein may be used to form an autologous valve in any vein suffering from chronic venous insufficiency, including but not limited to superficial veins and deep veins. As shown in FIG. 4, valve creation device 316 is not required to be placed adjacent to the incompetent valve but rather may be implanted at any location along vein 400. However, in an embodiment, the target location may be adjacent to the valve leaflets of the incompetent valve.

FIG. 4 illustrates how valve creation device 316 utilizes autologous vein tissue to form a new valve by forcing together the opposing portions of the vessel wall. Once implanted, contact portion 319 of valve creation device 316 engages the outer surface of a vessel wall of vein 400 at a first location, and contact portion 323 of valve creation device 316 engages the outer surface of the vessel wall of vein 400 at an opposing location of the vein, or approximately 180 degrees away from the first location. Particularly, sharpened or pointed tips 328, 330 at the ends of wire-like structure 317 pierce and penetrate through opposing portions of the vessel wall of vein 400. As shown in the cross-section of FIG. 4A, contact portion 319 and contact portion 323 move toward each other and exert a clamping or pinching force onto the opposing walls of vein 400 to press the opposing walls of vein 400 together and substantially closes lumen 402 of vein 400, thereby preventing or at least significantly reducing retrograde blood flow or reflux. The configuration, length, and width of contact portions 319, 323 determine how much of the vein wall is forced together.

Once implanted in vein 400, the new valve created by valve creation device 316 operates as a one-way valve that allows blood to flow in an antegrade direction and controls backflow through lumen 402 of vein 400, thereby seamlessly replacing the role of an incompetent native valve. In its closed configuration shown in FIG. 4, valve creation device 316 firmly forces opposing portions of the vein wall together to prevent gravitational or retrograde blood flow $R_F$ from backflowing through the newly created valve. In an embodiment, valve creation device 316 can withstand backpressure, i.e., a pressure gradient in the proximal to distal direction, of 300 mmHg with less than 1.0 mL/min of leakage. When antegrade blood flow $A_F$ overcomes the biasing spring force or mechanical memory of valve creation device 316 and pushes or forces apart contact portions 319, 323 of valve creation device 316, the new valve achieves the open valve configuration shown in FIGS. 5 and 5A and antegrade blood flows through the new valve. More particularly, blood flow pressure builds up on the inflow or distal side of the new valve when it is in the closed configuration shown in FIG. 4 until the point at which the pressure pushing outward against the inside surfaces or walls of the vessel exceeds the closing biasing force of valve creation device 316 pushing against the outer surface of the vessel. Valve creation device 316 then opens up, allowing the vein walls to separate and blood to flow antegrade across the new valve. The movement of antegrade blood flow across the new valve results in a drop or relief of pressure, and the biasing spring force or mechanical memory of valve creation device 316 takes over and closes valve creation device 316 thus preventing the backflow of blood.

More specifically, in order for blood to flow through a venous valve, there must be a force propelling the blood. This force is the pressure gradient or differential $\Delta P$, which is the difference in blood pressure occurring across the valve between the inflow or distal side of the valve and the outflow or proximal side of the valve. When pumped blood is advanced through vein 400 during normal circulation, the pressure gradient driving venous blood flow back to the heart is quite low. Native venous valves typically open with less than a 5 mm Hg pressure gradient. Thus, valve creation device 316 preferably opens under the same pressure gradients. In an embodiment, valve creation device 316 is forced into the open configuration in which the device is sufficiently spread apart to allow blood flow through the new valve and consequently lumen 402 of vein 400 in response to a 5 mm Hg pressure gradient. In another embodiment, valve creation device 316 opens in response to a 2 mmHg pressure gradient. Under certain higher pressure gradients, valve creation device 316 may significantly spread apart such that the new valve approaches a tubular or cylindrical cross-section. However, contact portions 319, 323 of valve creation device 316 need only be radially separated to a point sufficient to allow flow through the new valve, i.e., vein 400, and thus the new valve may have an hourglass shape when valve creation device 316 is in the open configuration. Generally, valve creation device 316 will achieve a valve open configuration that permits a flow of blood through the new valve at a rate of about 0.25 L/min to about 5 L/min.

Figure 25B:
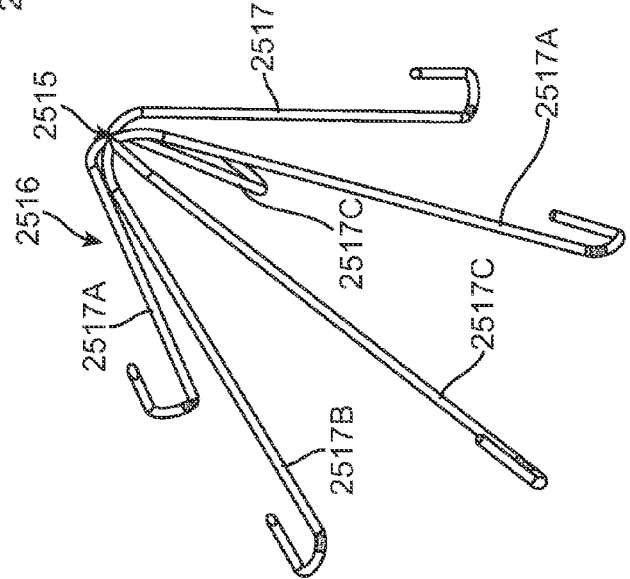
FIGS. 25A and 25B are perspective views of a valve creation device according to another embodiment hereof.
Figure 25A:
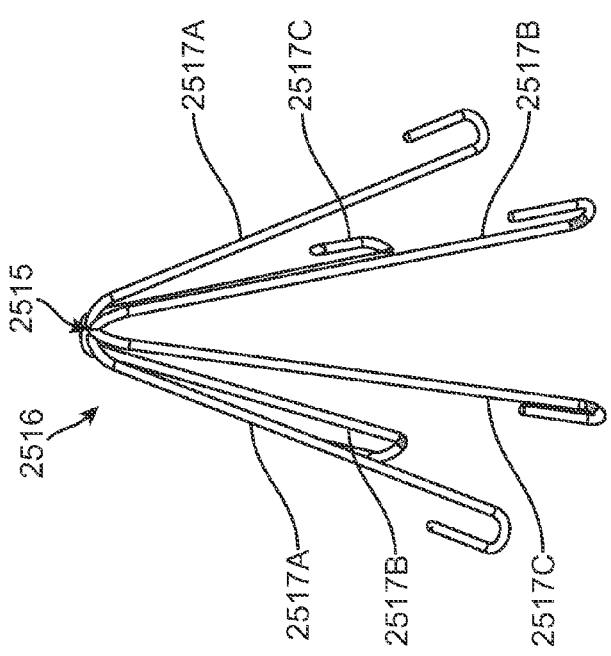

In the embodiment depicted in FIGS. 3-4 having contact portions 319, 323 located at opposing locations within the vein, valve creation device 316 has a substantially flat longitudinally extending structure when positioned in the vein. However, in another embodiment shown in FIGS. 25A and 25B, a valve creation device 2516 has a substantially conical structure when in the open configuration by including multiple V-shaped wire-like structures 2517A, 2517B, and 2517C, each having closed and open configurations similar to wire-like structure 317 as described above. Wire-like structures 2517A, 2517B, and 2517C are oriented such that three sets of contact portions are located around the circumference of the vein. The multiple wire-like structures are secured together at least at a single overlapping point or apex 2515 on the biasing members. With three sets of contact portions positioned around the circumference of the vein more complete closure of the lumen of the vein may be had when the opposing portions of the vessel wall are forced or gathered together by each wire-like structure 2517A, 2517B, and 2517C of valve creation device 2516. Although FIGS. 25A and 25B illustrate valve creation device 2516 having three wire-like structures 2517A, 2517B, and 2517C for a resulting six contact portions located around the circumference of the vessel wall, it should be understood that a valve creation device in accordance with embodiments hereof may include a greater number or lesser number of wire-like structures and corresponding sets of contact portions.

In the preset closed configuration valve creation device 316 has a resistance to opening that may depend on several factors in addition to the resilient material from which it is formed, including material stiffness of valve creation device 316, material thickness of valve creation device 316, and/or the geometry of valve creation device 316. By manipulating these factors, valve creation device 316 may be designed to obtain an open configuration under select pressure gradients such that the valve creation device will open at a particular implantation site within the vasculature. For example, a thinner wire-like structure 317 is less stiff and therefore has less resistance to opening than a thicker wire-like structure 317 of the same material. However, wire-like structure 317 must have a sufficient thickness and closing force to cause the opposing vessel walls to be forced together. Stiffness refers to the resistance of an elastic body to deflection or deformation by an applied force. In an embodiment, manufacturing or processing steps may be employed in order to alter the stiffness, i.e., resistance to deflection or deformation of wire-like structure 317. For example, heat treatment or irradiation (for a polymer wire) may be employed to alter the modulus of elasticity of the material of wire-like structure 317.

Figure 6:
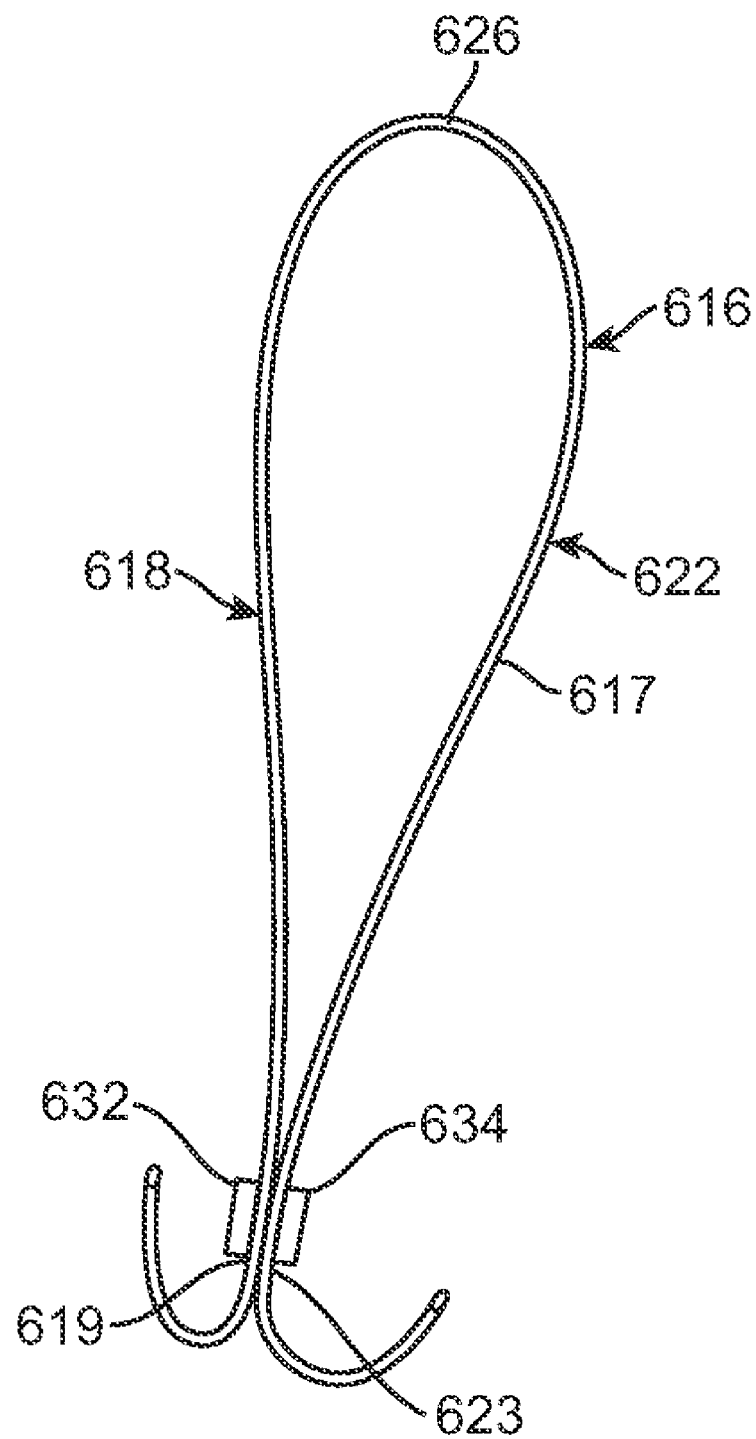
FIG. 6 is a perspective view of a valve creation device according to another embodiment hereof.

In embodiments hereof, magnets may be utilized to effect and/or enhance closure of a valve creation device in accordance herewith. For example, FIG. 6 shows a valve creation device 616 formed from a wire-like structure 617, the device having a first leg 618, a second leg 622, and a curved connector 626 extending between the first and second legs. Alternatively, in an embodiment, first leg 618 and second leg 622 may be connected together by a hinge (not shown). A first magnet 632 is located at a contact portion 619 of first leg 618 and a second magnet 634 is located at a contact portion 623 of second leg 622. Magnets 632, 634 are oriented on wire-like structure 617 to be attracted to each another so that contact portions 619, 623 firmly press together in the closed configuration of valve creation device 616 shown in FIG. 6 and once implanted with valve creation device 616 within a vein will operably force opposing portions of the vessel wall of the vein together. Valve creation device 616 holds the opposing portions of the vein wall forced together in the absence of a pressure differential while sufficient antegrade blood flow will operate to push apart first and second legs 618, 622 of valve creation device 616 by exceeding the magnetic force of magnets 632, 634. In one embodiment, magnets 632, 634 may range in diameter between 0.5 mm to 2.5 mm in diameter, may have a thickness less than 0.125 inches or 3.175 mm, and have a magnetic force between 0.0182 to 0.0455 lbs. Magnets 632, 634 may be positioned on wire-like structure 617 to abut extravascularly or intravascularly when the valve creation device is implanted in vivo. If placed intravascularly, magnets 632, 634 may be coated or covered with a biocompatible material such as parylene. Magnets 632, 634 may be attached to wire-like structure 617 by a biocompatible adhesive or other suitable attachment mechanism. In the described embodiment, magnets 632, 634 alone function to pull legs 618, 622 together and close valve creation device 616. In another embodiment, magnets 632, 634 may be used on valve creation device 316 described above such that biasing member 326 aids in closing, or on any valve creation device of a resilient material using a biasing member described below, to enhance closure thereof.

In another embodiment, closure of the vessel lumen by a valve creation device may be enhanced via the use of expandable loops on the valve creation device that increase surface contact or coverage on the outer surface of the vein wall to operably push more vein tissue together. FIG. 7 shows a side view of a valve creation device 716 having a first leg 718, a second leg 722, and a biasing member 726 attached to and extending between the first and second legs. Sharpened or pointed tips 728, 730 at the ends of first and second legs 718, 722, respectively are used to pierce and penetrate through opposing portions of the vessel wall of the vein. Rather than straight linear contact portions as shown above in the embodiment of FIG. 3, first and second legs 718, 722 include expandable loops 736, 738, along respective end portions 720, 724 thereof, which define diamond-shaped contact portions 719, 723. As shown in FIGS. 8A and 8B, which illustrate valve creation device 716 implanted within a vein 700, expandable loops 736, 738 cover a greater surface area on the outer surface of the vein wall so that contact portions 719,723 operably push more tissue together and enhance the backflow prevention of vein creation device 716. As such the clamping or pinching force of expandable loops 736, 738 is distributed along a greater surface area of the vessel wall. Expandable loops 736, 738 are formed of a superelastic or resilient material that self-expands to its preset memory configuration after delivery and deployment of valve creation device 716 within vein 700. During delivery within vein 700, expandable loops 736, 738 would be straightened into a delivery configuration by a retractable delivery sheath or other mechanism. Once positioned at the treatment site, valve creation device 716 is deployed and expandable loops 736, 738 pass through the vessel wall of vein 700 after respective pointed tips 728, 730 create an opening or passageway there through. During this initial implantation step, the vessel wall of vein 700 straightens or compresses expandable loops 736, 738 such that they can be passed there through.

In another embodiment, closure of the vessel lumen within the vein may be enhanced via the use of multiple fingers that extend from each leg of the valve creation device and operate to grab the outer surface of the vessel and force opposing portions of the vein wall inwardly. More particularly, FIG. 12 shows a valve creation device 1216 in its preset closed configuration formed from a wire-like structure 1217 of a resilient material, the device having a first leg 1218, a second leg 1222, and a biasing member 1226 extending between the first and second legs. As best shown in FIG. 13A, a set of two curved extensions or fingers 1237A, 1237B extend outwardly in opposite directions from a distal end 1235 of first leg 1218 in a plane perpendicular to a longitudinal axis $L_A$ of valve creation device 1216. Finger 1237A has a distal end 1233A, and finger 1237B has a distal end 1233B. During delivery within a vein, fingers 1237A, 1237B may be straightened into a delivery configuration by a retractable delivery sheath or other mechanism. Once positioned at the treatment site, valve creation device 1216 is deployed and fingers 1237A, 1237B pass through the vessel wall of the vein. During this initial implantation step, the vessel wall of the vein maintains fingers 1237A, 1237B in the straightened delivery configuration such that they can be passed there through. Once distal end 1235 of first leg 1218 passes through the vessel wall, fingers 1237A, 1237B self-expand to their preset memory configuration and wrap around the outer surface of the vein, as best illustrated in the cross-sectional view of FIG. 13, which shows valve creation device 1216 in the open configuration implanted within vein 1300. As such, fingers 1237A and 1237B extend around and press against a substantial portion of the vessel wall. Similarly, a set of two curved extensions or fingers 1239A, 1239B extend outwardly in opposite directions from a distal end 1241 of second leg 1222 in a plane perpendicular to longitudinal axis $L_A$ of valve creation device 1216. Finger 1239A has a distal end 1243A, and finger 1239B has a distal end 1243B. During delivery within a vein, fingers 1239A, 1239B may be straightened into a delivery configuration by a retractable delivery sheath or other mechanism. Once positioned at the treatment site, valve creation device 1216 is deployed and fingers 1239A, 1239B pass through the vessel wall of the vein. During this initial implantation step, the vessel wall of the vein maintains fingers 1239A, 1239B in the straightened delivery configuration such that they can be passed there through. Once distal end 1241 of second leg 1222 passes through the vessel wall, fingers 1239A, 1239B self-expand to their preset memory configuration and wrap around the outer surface of the vein. As such, fingers 1239A and 1239B extend around and press against a substantial portion of the vessel wall.

Thus, as shown in the cross-sectional view of FIG. 13, fingers 1237A, 1237B, 1239A, and 1239B collectively extend around and press against a substantial portion of the outer circumference of the vein wall. Each finger acts to push the vessel wall inwards to close the lumen of the vein when valve creation device 1216 returns to the preset closed configuration shown in FIG. 12. More particularly, as indicated by the directional arrows in phantom on FIG. 13, distal end 1233A of finger 1237A and distal end 1233B of finger 1237B operate as a first set of contact portions of valve creation device 1216 that are biased or pressed toward each other to press opposing portions of the vessel wall together when valve creation device 1216 is in the preset closed configuration. Similarly, distal end 1243A of finger 1239A and distal end 1243B of finger 1239B operate as a second set of contact portions of valve creation device 1216 that are biased or pressed toward each other to press opposing portions of the vessel wall together when valve creation device 1216 is in the preset closed configuration. Further, distal end 1235 of first leg 1218 and distal end 1241 of second leg 1222 operate as a third set of contact portions of valve creation device 1216 that are biased or pressed toward each other to press opposing portions of the vessel wall together when valve creation device 1216 is in the preset closed configuration. Collectively, the vessel wall is forced together in multiple locations which may more completely close the lumen of the vein, thereby enhancing backflow prevention through the newly created valve.

Figure 9:
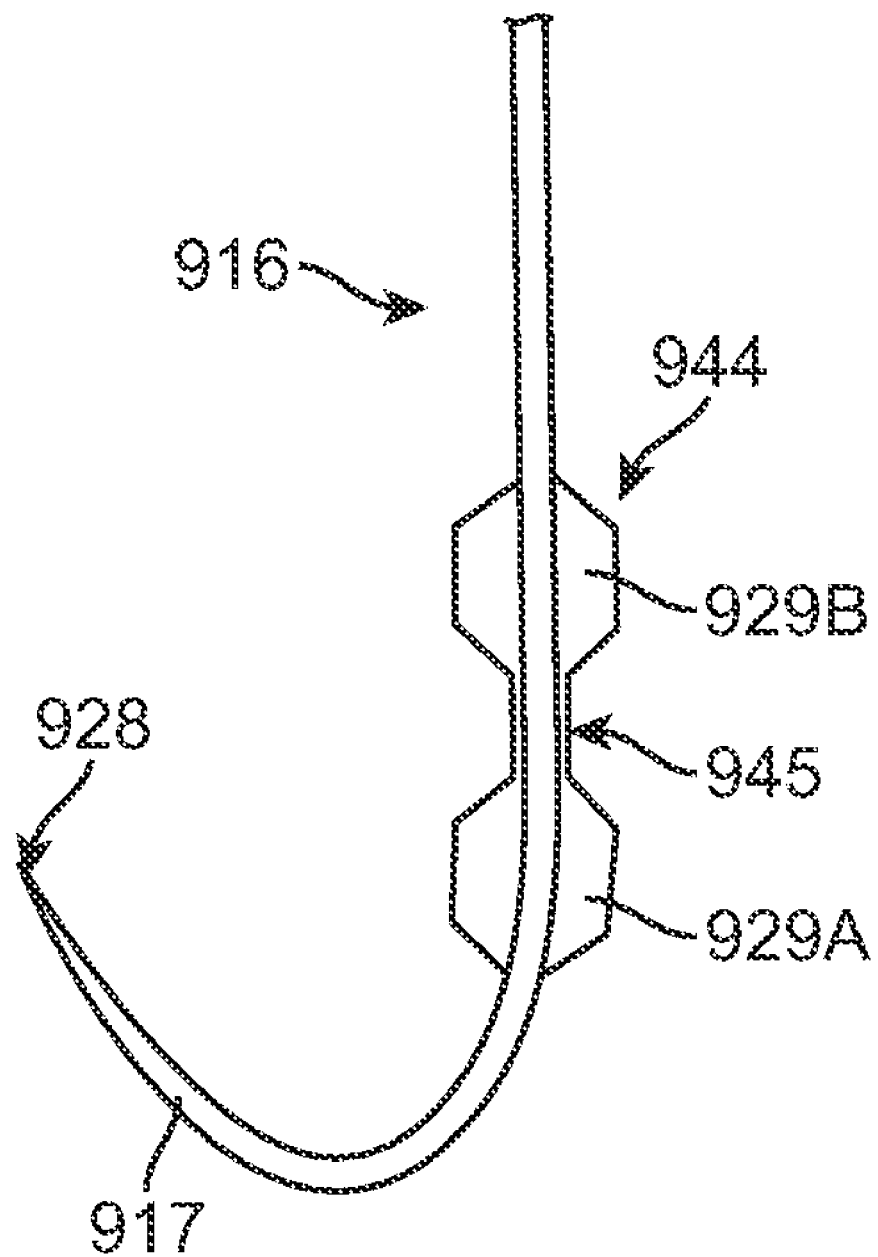
FIG. 9 is a side view of a portion of a valve creation device according to another embodiment hereof.

FIG. 9 illustrates a portion of a valve creation device 916 in accordance with another embodiment hereof for minimizing the risk of blood leaking through the vein wall after the valve creation device is implanted. To prevent extravascular leakage of blood through the point(s) at which valve creation device 916 passes through the vessel wall, a seal 944 is attached to wire-like structure 917. Seal 944 may be of any suitable material such as an elastomeric material, a natural or synthetic rubber, silicone, or a collagen foam plug. Seal 944 may be attached to wire-like structure 917 by a biocompatible adhesive or other suitable attachment mechanism. Seal 944 acts to press against one or more surface(s) of the vessel wall after pointed tip 928 of wire-like structure 917 pierces through the vein wall. In the embodiment of FIG. 9, seal 944 has a dumbbell configuration with an intermediate portion 945, which has a first or reduced diameter, being sandwiched between end portions 929A, 929B, which have a second or flared diameter that is greater than the first or reduced diameter of intermediate portion 945. When placed in situ, intermediate portion 945 will extend through the vessel wall with end portion 929A pressing or sitting against the outer surface of the vessel wall and end portion 929B pressing or sitting against the inner surface of the vessel wall. In an embodiment (not shown), the seal may have an annular or donut-shaped configuration similar to an O-ring or washer. The annular seal would be attached to the wire-like structure 917 in a location such that it is located against the inner surface of the vessel wall or the outer surface of the vessel wall when placed in situ.

Another embodiment of a valve creation device 1016 is shown in FIGS. 10-11. Valve creation device 1016 acts as a support framework to open and close opposing portions of the vessel wall of a vein in response to antegrade and retrograde blood flow to thereby mimic venous valve operation for treating chronic venous insufficiency. Similar to the above embodiments, valve creation device 1016 is an implantable prosthesis formed from a wire-like or tubular structure 1017 of a resilient material and includes a first leg 1018, a second leg 1022, and a biasing member 1026 extending between first leg 1018 to second leg 1022. In this embodiment, the legs 1018, 1022 of valve creation device 1016 are each configured to engage the vessel wall of the vein with a set of attachment joints. First leg 1018 has a first attachment joint 1020 and a third attachment joint 1021 separated by a curved segment 1013 defining a contact portion 1019, and second leg 1022 has a second attachment joint 1024 and a fourth attachment joint 1025 separated by a curved segment 1013 defining a contact portion 1023, each of attachment joints 1020, 1021, 1024, 1025 is configured to engage the vessel wall of the vein. In one embodiment, attachment joints 1020, 1021, 1024, 1025 include anchors attached to wire-like structure 1017 that lodge within the vessel wall to securely fix valve creation device 1016 within the vein. The anchors embed midway through the vessel wall, such as through some or the entire intimal layer and some or the entire medial layer of the vein wall, rather than penetrate there though. The anchors avoid penetrating through the vessel wall to minimize the risk of blood leaking through the vein wall. Although the anchors are illustrated as smooth surfaced round balls in FIGS. 10-11, the anchors may include pointed or spiked barbs or tines such as those depicted in FIGS. 21-24, or may have other configurations suitable for lodging within the vessel wall. In another embodiment, the anchors penetrate through the vessel wall to increase pulling or pinching the vein wall together. In addition to securing valve creation device 1016 in the vein, the anchors simultaneously act as a sealing mechanism to prevent blood loss through the penetrated vessel wall.

Valve creation device 1016 is operable to alternate between a preset closed configuration that in vivo results in the valve closed configuration shown in FIG. 10 and an open configuration that in vivo achieves the valve open or flow configuration shown in FIG. 11. In the preset closed configuration, first attachment joint 1020 is biased toward third attachment joint 1021 on first leg 1018 and second attachment joint 1024 is biased toward fourth attachment joint 1025 on second leg 1022 such that first leg contact portion 1019 is biased toward and/or contacts second leg contact portion 1023. However, valve creation device 1016 is deployed within a vein 1000 in its open configuration, such that attachment joints 1020, 1021, 1024, and 1025 engage the vessel wall of vein 1000 as shown in FIG. 11. The delivery of valve creation device 1016 is described in further detail below with respect to FIGS. 21-24. After valve creation device 1016 is released from the delivery system, it reverts back to its preset closed configuration shown in FIG. 10 due to the restoring spring force of wire-like structure 1017. As valve creation device 1016 closes, attachment joints 1020 and 1021 located along first leg 1018 move toward each other causing vein wall segment 1046 to fold inwardly toward the opposing vein wall. Similarly, attachment joints 1024 and 1025 located along second leg 1022 move toward each other causing vein wall segment 1047 to fold inwardly toward the opposing vein wall. As noted above, contact portion 1019 of first leg 1018 and contact portion 1023 of second leg 1022 also move toward each other as valve creation device 1016 returns to the preset closed configuration. Vein wall segment 1046 and vein wall segment 1047 are thereby pushed together until contact portion 1019 of first leg 1018 and contact portion 1023 of second leg 1022 abut as shown in FIG. 10, such that the lumen of the vein is substantially closed. The restoring force of valve creation device 1016 due to the resilient material of wire-like structure 1017 thus draws vein wall segments or flaps 1046, 1047 together to create a new valve within the vein. In situ, antegrade blood flow acts to forcibly separate contact portion 1019 of first leg 1018 and contact portion 1023 of second leg 1022 to achieve the valve open configuration shown in FIG. 11 and to allow flow through the new valve. When blood flow through the vein changes direction, i.e., retrograde blood flow occurs due to changing pressure differentials across the new valve, valve creation device 1016 reverts back to the preset closed configuration to thereby return the new valve to the valve closed configuration and prevent blood from backflowing through the new valve.

In an embodiment, valve creation device 1016 extends longitudinally within the vein such that attachment joints 1020, 1021, 1024, 1025 are in the same longitudinal plane when valve creation device 1016 is implanted within the vein. In another embodiment, attachment joints 1020 and 1024 extend within a first longitudinal plane when valve creation device 1016 is implanted within the vein, and attachment joints 1021 and 1025 extend within a different longitudinal plane. Further, in another embodiment (not shown), the valve creation device may include two or more wire-like structures, each having closed and open configurations similar to wire-like structure 1017 as described above, that are oriented such that additional sets of contact portions are located around the circumference of the vein. Multiple sets of contact portions positioned around the circumference of the vein may result in more complete closure of the vein lumen when the opposing portions of the vessel wall are forced or gathered together. For example, in an embodiment a valve creation device may include a first wire-like structure 1017 and a second wire-like structure 1017 having an orientation rotated approximately ninety degrees from the first wire-like structure 1017, with the first and second wire-like structures secured together at a single overlapping point or apex on biasing members 1026.

The valve prostheses described herein are preferably delivered in a percutaneous, minimally invasive manner and may be delivered by any suitable delivery system. Referring now to FIGS. 14-17, a method of percutaneously placing a valve creation device within a vein to create a valve from autologous vein tissue according to an embodiment hereof is described. Lumenal access to the venous vasculature is obtained using standard percutaneous techniques, such as the Seldinger technique as would be understood by one of ordinary skill in the art. Access to the vasculature may be achieved through a branch of the femoral vein, or alternatively, may be achieved through a branch of a peripheral vein, such as but not limited to the subclavian vein, the popliteal vein, or the greater saphenous vein. A guidewire (not shown) is maneuvered to a treatment site within vein 1400 where a new valve is to be created. The treatment site may be located upstream or downstream of leaflets of an insufficient native valve. Valve prostheses described herein may be delivered to the treatment site in an antegrade or retrograde manner. In one embodiment, delivery of the valve creation device is in an antegrade direction such that the valve creation device passes forwardly through native valves located within the vein in route to the treatment site. A balloon catheter 1450 with valve creation device 316, as described above with reference to FIG. 3, mounted thereon is loaded into a retractable sheath 1448 that surrounds and substantially straightens the valve creation device 316, which eases advancement thereof through the vasculature to the treatment site within a body vessel. Sheath 1448, balloon catheter 1450 and valve creation device 316 are then tracked over the guidewire through the vasculature to the treatment site, as shown in FIG. 14. Retractable sheath 1448 is movable in a longitudinal direction along and relative to balloon catheter 1450 and extends to a proximal portion of the delivery system where it may be controlled via an actuator (not shown), such as a handle. When the actuator is operated, retractable sheath 1448 is proximally retracted over catheter 1450.

Valve creation device 316 may be secured to balloon 1452 with a connector 1454. Connector 1454 may be a breakable restraining member that uncouples the valve creation device 316 when balloon is inflated to a predetermined diameter. The breakable restraining member may be formed from an elastomeric material such as polyurethane or pelethane and may include a perforation or line of weakness 1456 that would cause the elastomeric material to split in a preferred direction when balloon 1452 reaches a particular diameter. The breakable restraining member may be an annular ring or straight band that is placed over valve creation device 316 mounted on balloon 1452, and is attached to balloon 1452 in at least one spot to prevent the breakable restraining member from dislodging and/or embolizing from balloon 1452 after valve creation device 316 is deployed. In another embodiment, connector 1454 may be an annular or straight thin metal element that holds valve creation device 316 onto balloon 1452 until a current is applied to dissolve the thin metal element, thereby releasing valve creation device 316 from balloon 1452 with an electrolytic detachment technique. The thin metal element may or may not include a line of weakness 1456. Electrolytic detachment techniques are known, for example, for delivering and detaching coils at an occlusion or aneurysm site. Thin metal elements and detachment techniques therefore that may be adapted for use in embodiments hereof are described in U.S. Pat. Nos. 5,569,245 to Guglielmi et al. and 5,624,449 to Pham et al., which are incorporated by reference herein in their entirety.

Once valve creation device 316 is properly positioned and it is desired to deploy valve creation device 316, sheath 1448 and valve creation device 316 may be moved relative to each other such that valve creation device 316 is released from sheath 1448 and allowed to assume its preset configuration as shown in FIG. 15. To cause the relative motion between sheath 1448 and valve creation device 316, valve creation device 316 may be distally advanced while sheath 1448 is held in place so that valve creation device 316 is essentially pushed out of the distal exit port of sheath 1448, or sheath 1448 may be retracted in a proximal direction while valve creation device 316 is held in place so that valve creation device 316 is essentially exposed, or a combination thereof. Once valve creation device 316 exits sheath 1448, the ends of valve creation device 316 elastically flare open and assume a curve as valve creation device 316 returns to its preset closed configuration due to the inherent spring restorative force of the valve creation device.

Balloon 1452 is then at least partially inflated to push pointed tips 328, 330 of valve creation device 316 into and through the vessel wall as shown in FIG. 16 and to position contact portions 319, 323 against an outer surface of the vessel wall of vein 1400 as shown in FIG. 17. If a breakable restraining member is used as connector 1454 to secure valve creation device 316 to balloon 1452, inflation of the balloon 1452 to a predetermined diameter will break apart or open connector 1454 along line of weakness 1456 thereby uncoupling valve creation device 316 from balloon 1452 as shown in FIG. 16. Alternatively, a thin dissolvable metal element is used as connector 1454 to secure valve creation device 316 to balloon 1452, a current is applied to dissolve the thin metal element and thereby uncouple valve creation device from balloon 1452 (not shown).

Once the valve creation device 316 is fixed to opposing portions of the vessel wall of vein 1400 and valve creation device 316 is uncoupled from balloon 1452, balloon catheter 1450 may be deflated and removed from the patient. As described above with respect to FIG. 4, first contact portion 319 of valve creation device 316 engages the vessel wall at a first location, and second contact portion 323 of valve creation device 316 engages the vessel wall at an opposing location, or approximately 180 degrees away from the first location. With balloon catheter 1450 removed, valve creation device 316 reverts to its preset closed configuration thereby pulling the opposing portions of the wall of vein 1400 together to substantially close the lumen of vein 1400 as shown in FIG. 17. In such a manner, percutaneously delivered valve creation device 316 utilizes autologous vein tissue to form a new valve by forcing together opposing portions of the vessel wall.

In an embodiment, vein 1400 is a deep vein that is surrounded in part by musculature tissue. Prior to implanting valve creation device 316, the outer surface or circumference of the vein wall may be extravascularly separated from the muscle so that valve creation device 316 may operate to pull the vein wall together. Any suitable method may be utilized to separate the vein wall from the surrounding musculature tissue. In one example, an inflatable balloon extravascularly placed between the vein wall and muscle may be expanded to dilate the space between the vein wall and the surrounding musculature tissue and cause the separation therebetween.

In an embodiment shown in FIG. 14A, balloon 1452A may be tapered such that a proximal end portion 1451 has a larger diameter than a distal end portion 1453 when balloon 1452A is inflated. Omitted from FIG. 14A for clarity, valve creation device 316 is mounted on the smaller distal end portion 1453 of balloon 1452A. When inflated, the larger proximal end 1451 of balloon 1452A operates to center the delivery device within the vein when valve creation device 316 is deployed. In another embodiment shown in FIG. 14B, the delivery device may include a second balloon 1458 proximal to a balloon 1452B for centering the delivery device during deployment of valve creation device 316 (omitted from FIG. 14B for clarity), which is mounted on balloon 1452B as described above with respect to balloon 1452 of FIG. 14.

Figure 20:
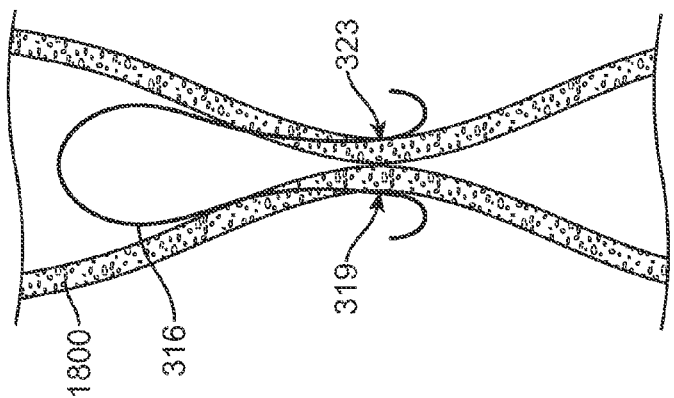
FIGS. 18, 19, and 20 are schematic representations of another method of percutaneously placing a valve creation device within a vein to create a valve from autologous vein tissue according to an embodiment hereof.
Figure 19:
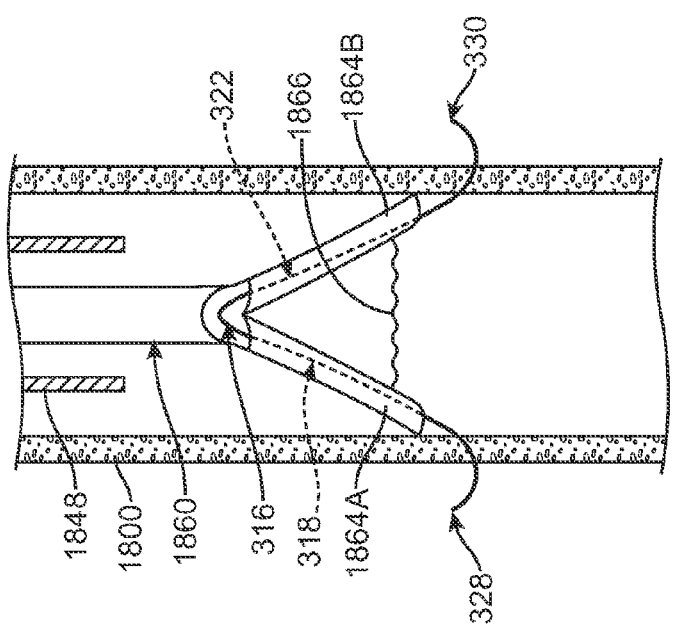
Figure 18:
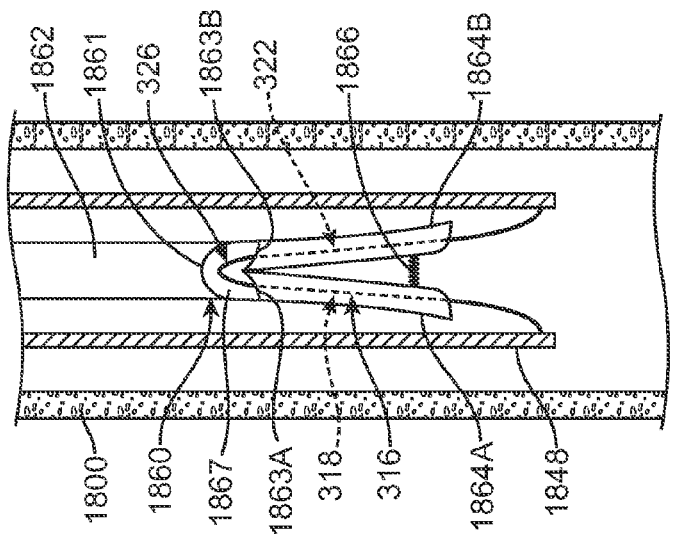
Figure 18A:
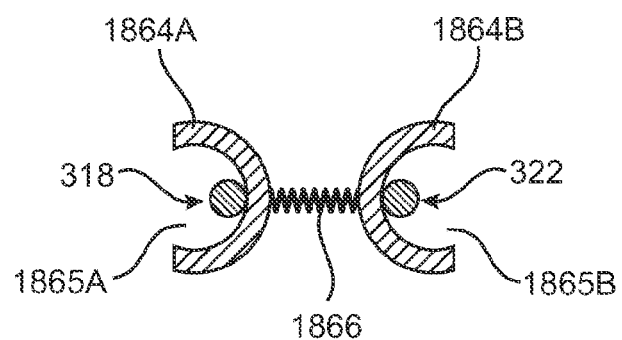
FIG. 18A is an end view of the delivery system of FIGS. 18 and 19, with the legs of the valve creation device loaded therein.
Figure 18B:
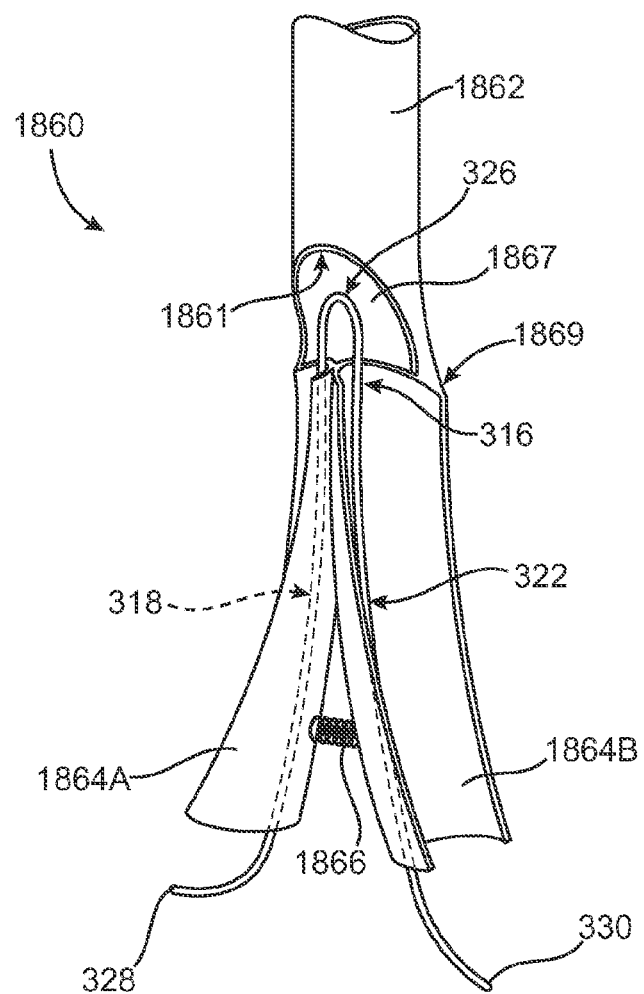
FIG. 18B is a perspective view of the delivery system of FIGS. 18 and 19, with the valve creation device loaded therein.

Referring now to FIGS. 18-20, another method of percutaneously placing a valve creation device within a vein to create a valve from autologous vein tissue according to an embodiment hereof is described. In this embodiment, valve creation device 316, as described above with reference to FIG. 3, is mounted onto a distal end of a delivery catheter 1860. Referring to FIGS. 18, 18A and 18B, delivery catheter 1860 includes an elongated proximal trunk or tubular shaft 1862 having a proximal end that may be attached to a luer or hub (not shown) and a distal end attached to first and second distal branches or arms 1864A, 1864B, respectively, via a junction 1869. First and second distal arms 1864A, 1864B separately and independently extend from the distal end of proximal shaft 1862. Junction 1869 is a transition area between proximal shaft 1862 and distal arms 1864A, 1864B. In one embodiment, proximal shaft 1862 and distal arms 1864A, 1864B may be separate components that are welded, fused, bonded, or otherwise joined together. In another embodiment, if the same material is used for proximal shaft 1862 and distal arms 1864A, 1864B, then catheter 1862 may be formed via extrusion resulting in one continuous structure. Each arm 1864A, 1864B has a generally C-shaped or semicircular transverse cross-section along its length, with an open area 1865A, 1865B of each C-shaped arm 1864A, 1864B, respectively, being oriented outward as shown in FIG. 18A. FIG. 18A is an end view of distal arms 1864A, 1864B of delivery catheter 1860 having legs 318, 322 of valve creation device 316 loaded therein, with the vein and delivery sheath removed for clarity. In an embodiment, the C-shaped cross-section of each arm 1864A, 1864B may be between 25% and 75% of the circumference of a circle. Each arm 1864A, 1864B may be longitudinally tapered such that delivery catheter 1860 may be disengaged after valve creation device 316 is deployed as will be explained in more detail herein. For example, as shown in FIG. 18B, the proximal ends of each arm 1864A, 1864B are approximately 25% of a circle such that the top edge of the arm barely extends over valve creation device 316 and the C-shaped cross-section of each arm 1864A, 1864B gradually increases until the distal ends of each arm 1864A, 1864B are approximately 50% of a circle. In one embodiment shown in FIG. 18B, distal arms 1864A, 1864B may have a length that is shorter than legs 318, 322 of valve creation device 316 loaded therein such that pointed tips 328, 330 extend beyond the distal ends of arms 1864A, 1864B, respectively. In another embodiment (not shown), distal arms 1864A, 1864B may have a length that is approximately equal to or greater than legs 318, 322 of valve creation device 316 loaded therein. Distal arms 1864A, 1864B are connected with a self-expanding spring element 1866 that spans between arms 1864A, 1864B. Spring element 1866 may span between a proximal portion, a middle portion, or a distal portion of arms 1864A, 1864B.

At the distal end thereof, a top portion of proximal shaft 1862 has a concave curved top edge 1861. Similarly, at the proximal ends thereof, a side portion of each distal arm 1864A, 1864B have a concave curved top edge 1863A, 1863B, respectively. Collectively, these carved out portions form a side opening or port 1867 in catheter 1860 at junction 1869. Port 1867 is in fluid communication with open areas 1865A, 1865B of C-shaped distal arms 1864A, 1864B such that catheter 1860 has a continuous path or track formed thereon, as will be described in more detail herein. Valve creation device 316 in its preset closed configuration is mounted within catheter 1860 such that legs 318, 322 of valve creation device 316 are loaded through open areas 1865A, 1865B to sit against the outer surfaces of distal arms 1864A, 1864B, as best shown in the end view of FIG. 18A, and such that biasing member 326 of valve creation device 316 is positioned adjacent to or within port 1867, as best shown in the perspective view of FIG. 18B.

With reference to FIG. 18, catheter 1860 with valve creation device 316 mounted thereon are loaded into a retractable sheath 1848 that surrounds distal arms 1864A, 1864B and compresses spring element 1866 to hold valve creation device 316 in a delivery configuration, which eases advancement thereof through the vasculature to the treatment site within a body vessel. Retractable sheath 1848 is movable in a longitudinal direction along and relative to delivery catheter 1860 and extends to a proximal portion of the delivery system where it may be manipulated by a clinician to be proximally retracted over catheter 1860 when valve creation device 316 is to be deployed. Sheath 1848 and catheter 1860 with valve creation device 316 loaded thereon are percutaneously introduced and delivered through the vasculature to the treatment site as described above. The treatment site may be located upstream or downstream of leaflets of an insufficient native valve.

Once valve creation device 316 is properly positioned, sheath 1848 of the delivery system is proximally retracted as shown in FIG. 19 to deploy valve creation device 316. Upon retraction of sheath 1448, distal arms 1864A, 1864B are released to swing open via self-expanding spring element 1866, which also pushes the pointed tips 328, 330 of valve creation device 316 into and through the vessel wall as shown in FIG. 19. After pointed tips 328, 330 have been deployed through the vessel wall, the compressed spring element 1866 continues to return to or resume its preset extended configuration shown in FIG. 19, which then causes distal arms 1864A, 1864B to push the hooked end portions of valve creation device 316 through the vessel wall such that contact portions 319, 323 contact and eventually bear against the outer surface of the vessel wall as shown in FIG. 20. The restoring force of spring element 1866 is stronger than the inherent spring force or mechanical memory of valve creation device 316 and is sufficient to deploy the device through the vessel wall. In an embodiment (not shown), catheter 1860 may include an inflatable balloon proximal to distal arms 1864A, 1864B for centering the delivery device during deployment of valve creation device 316.

Once legs 318, 322 of valve creation device 316 is fixed to opposing portions of the vessel wall of vein 1800, the catheter 1860 may be proximally retracted a short amount to disengage valve creation device 316 therefrom. More particularly, legs 318, 322 of valve creation device 316 may be disengaged from within distal arms 1864A, 1864B by sliding out of open areas 1865A, 1865B, respectively. Similarly, biasing member 326 of valve creation device 316 may exit or be disengaged from within catheter 1860 via port 1867. Proximal movement of catheter 1860 allows biasing member 326 to become disengaged by sliding over the longitudinally tapered configuration of each arm 1864A, 1864B. Since valve creation device 316 is secured within the vessel via pointed tips 328, 330 deployed through the vessel wall, the valve creation device 316 remains stationary while catheter 1860 is proximally retracted and essentially is slid off the deployed valve creation device 316. Open areas 1865A, 1865B of the C-shaped distal arms 1864A, 1864B and port 1867 thus collectively form an exit path or track that allows catheter 1860 to be separated from the deployed valve creation device 316.

After the deployed valve creation device 316 is disengaged from catheter 1860, sheath 1848 is then distally advanced to cover and re-constrain distal arms 1864A, 1864B therein so that catheter 1860 may be retracted and removed from the patient. With catheter 1860 removed, valve creation device 316 reverts to its preset closed configuration thereby pulling the opposing portions of the wall of vein 1800 together to substantially close the lumen of vein 1800 as shown in FIG. 20. In such a manner, percutaneously delivered valve creation device 316 thus utilizes autologous vein tissue to form a new valve by forcing together the opposing portions of the vessel wall.

FIGS. 21-24 illustrate the percutaneous delivery of valve creation device 1016, described above with reference to FIGS. 10 and 11. Referring to FIG. 21, balloon catheter 1450 with valve creation device 1016 mounted thereon is loaded into retractable sheath 1448 that surrounds and substantially straightens the valve creation device 1016. As described above, the valve creation device may be secured to balloon 1452 with a breakable restraining member (not shown) that uncouples the valve creation device 1016 when balloon 1452 is inflated to a predetermined diameter, or with a thin metal element (not shown) that holds the device until a current is applied to dissolve the thin metal element. Sheath 1448, balloon catheter 1450 and valve creation device 1016 are then tracked over the guidewire through the vasculature to a treatment site within a vein 1000.

Once valve creation device 1016 is properly positioned and it is desired to deploy valve creation device 1016, sheath 1448 and valve creation device 1016 may be moved relative to each other such that a distal portion of valve creation device 1016 is exposed or released from sheath 1448. As shown in FIG. 22, once valve creation device 1016 exits sheath 1448 distal attachment joints 1020, 1024 flare open and extend to the vessel wall to return valve creation device 1016 to its preset configuration. Balloon catheter 1450 may be slightly proximally retracted to secure attachment joints 1020, 1024 within the vessel wall.

Referring to FIG. 23, sheath 1448 is further retracted to expose the remainder of valve creation device 1016 and balloon 1452 is at least partially inflated to push proximal attachment joints 1021, 1025 of valve creation device 1016 into the vessel wall. Inflation of balloon 1452 thus expands valve creation device 1016 into its open configuration. As noted above, valve creation device 1016 is uncoupled from balloon 1452, either by breaking apart the restraining member due to the balloon inflation or by dissolving the thin metal element, and balloon catheter 1450 may then be deflated and removed from the patient. With balloon catheter 1450 removed, valve creation device 1016 reverts to its preset closed configuration shown in FIG. 24 due to the restoring spring force of valve creation device 1016 thereby drawing vein wall segments or flaps 1046, 1047 together to substantially close the lumen of vein 1000.

Although the valve creation devices are described herein as configured for percutaneous placement, it should be understood that the valve creation devices may alternatively be surgically implanted within a vein in a non-percutaneous manner and may be anchored to the vein in any suitable manner, such as via sutures, clips, or other attachment mechanisms.

As would be understood by one of skill in the art, an outside layer of the vein wall, called the adventitia, is made of collagen, vasa vasorum and nerve cells, whereas a middle layer of the vein wall, or media, is made of smooth muscle cells and an inside layer of the vein wall, or intima, is made up of endothelial cells that provide a nonthrombogenic surface for flowing blood. The inventors have found that the outside and middle layers of the vessel wall provide sufficient toughness for opposing portions of the vein wall to be forced together to form a new valve by a valve creation device in accordance with embodiments hereof without tearing or ripping. Further it is believed that the anatomy of the vein wall has sufficient strength to enable opposing portions of the vein wall to act as a new valve by being capable of withstanding repeated pulling apart and pushing together by a valve creation device in accordance with embodiments hereof. In addition, a further advantage of an implanted valve creation device in accordance with embodiments hereof is that the intimal layer of the vessel wall forms the blood-contacting surfaces of the new valve.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An implantable prosthesis for creating a venous valve of autologous tissue, the prosthesis comprising:
  a valve creation device including at least two contact portions that in a preset closed configuration forces opposing portions of a vein wall together so that the opposing portions of the vein wall are pressed together and sandwiched between the contact portions to substantially close a lumen of the vein and create a valve of autologous vein tissue to substantially prevent retrograde blood flow through the valve, wherein the valve creation device is configured to change shape and assume a temporary open configuration in which the contact portions and the opposing portions of the vein wall separate in response to antegrade blood flow through the vein to allow blood flow through the lumen of the vein.

2. The prosthesis of claim 1, wherein the at least two contact portions comprise a first contact portion and a second contact portion; wherein the valve creation device is a wire-like structure having a first leg with the first contact portion, a second leg with the second contact portion, and a segment extending between the first leg and the second leg and wherein the first and second contact portions are biased toward each other to operably force opposing portions of the vein wall together in situ so that the opposing portions of the vein wall are pressed together and sandwiched between the contact portions to substantially close the lumen of the vein and create the valve.

3. The prosthesis of claim 2, wherein the valve creation device attains the open configuration that allows antegrade blood flow through the valve in response to a pressure gradient and wherein the valve creation device returns to the preset closed configuration in the absence of the pressure gradient to prevent retrograde blood flow through the valve.

4. The prosthesis of claim 3, wherein the valve creation device attains the open configuration that allows antegrade blood flow through the valve in response to a pressure gradient between 2 mmHg and 25 mmHg.

5. The prosthesis of claim 2, wherein the segment extending between the first leg and the second leg is a biasing member having spring characteristics to press together the contact portions of the first and second legs of the valve creation device.

6. The prosthesis of claim 5, wherein the biasing member is a U-shaped curve and the first and second legs of the valve creation device are mirror images of each other.

7. The prosthesis of claim 5, wherein the biasing member includes an elongated straight member operable to span across the vessel lumen of the vein.

8. The prosthesis of claim 2, wherein the segment extending between the first leg and the second leg is integrally formed with the first and second legs such that the valve creation device is a unitary structure formed from a single piece of material.

9. The prosthesis of claim 2, wherein the first and second legs each have a pointed tip for piercing the vein wall.

10. The prosthesis of claim 9, wherein each pointed tip is at an end of a respective curved end portion of the first and second legs.

11. The prosthesis of claim 2, wherein at least one of the first leg or the second leg includes a seal attached thereto, wherein the seal is operative to prevent leakage through the vein wall.

12. The prosthesis of claim 11, wherein the seal has a dumbbell configuration with an intermediate portion having a first diameter sandwiched between end portions having a second diameter greater than the first diameter of the intermediate portion, wherein the intermediate portion is operable to extend through the vessel wall and the end portions sit against outer and inner surfaces of the vein wall.

13. The prosthesis of claim 2, wherein the valve creation device includes at least two wire-like structures that are secured together at a single overlapping point on the segments extending between the first legs and the second legs.

14. The prosthesis of claim 2, wherein a first magnet is attached to the first leg and a second magnet is attached to the second leg and wherein the magnets are oriented to be attracted to one another with a magnetic force sufficient to force the opposing portions of the vein wall together in situ to create the valve.

15. The prosthesis of claim 2, wherein the first and second contact portions of the first and second legs are self-expanding loops located along respective end portions of the first and second legs.

16. The prosthesis of claim 2, wherein the first leg has two curved fingers that extend in opposite directions from an end thereof and the second leg has two curved fingers that extend in opposite directions from an end thereof, wherein the curved fingers are substantially perpendicular to a longitudinal axis of the valve creation device.

* * * * *